United States Patent
Beyar et al.

(10) Patent No.: US 10,617,458 B2
(45) Date of Patent: Apr. 14, 2020

(54) MULTI-LAYER COMPOSITE MATERIAL BONE SCREW

(71) Applicant: Carbofix In Orthopedics LLC, Wilmington, DE (US)

(72) Inventors: Mordechay Beyar, Caesarea (IL); Oren Globerman, Kfar-Shemaryahu (IL)

(73) Assignee: Carbofix In Orthopedics LLC, Wilmington, DE (US)

( * ) Notice: Subject to any disclaimer, the term of this patent is extended or adjusted under 35 U.S.C. 154(b) by 934 days.

(21) Appl. No.: 14/757,523

(22) Filed: Dec. 23, 2015

(65) Prior Publication Data
US 2017/0181785 A1    Jun. 29, 2017

(51) Int. Cl.
*A61B 17/86* (2006.01)
*A61L 31/12* (2006.01)
(Continued)

(52) U.S. Cl.
CPC .......... *A61B 17/866* (2013.01); *A61B 17/864* (2013.01); *A61B 17/8635* (2013.01);
(Continued)

(58) Field of Classification Search
CPC .......... A61B 2017/00964; A61B 17/86; A61B 17/866; A61L 31/12; A61L 31/125
See application file for complete search history.

(56) References Cited

U.S. PATENT DOCUMENTS 3,630,253 A    12/1971   Sherman
3,995,092 A *  11/1976   Fuchs ............... B27D 1/04
                                              428/400

(Continued)

FOREIGN PATENT DOCUMENTS

CN    1170380    1/1998
CN    1324278    11/2001
(Continued)

OTHER PUBLICATIONS

European Search Report and the European Search Opinion dated May 25, 2016 From the European Patent Office Re. Application No. 15194868.4.
(Continued)

*Primary Examiner* — David W Bates

(57) ABSTRACT

Composite material screws and construction techniques are described comprising reinforcing fibers directed in different winding directions and/or angles at different layers (radial depths) of the screw. Optionally, the screw comprises composite material layers wound with fibers at both the pitch of the thread of the screw and at a steeper pitch (for example, about 45°). Optionally, an outer layer of the screw comprises a relative radiolucent construction and/or material, with a more radiopaque construction and/or material positioned underneath the outer layer such that at least a portion of the screw outline is delineated by a radioimaging technique (for example, fluoroscopy, CT, or MRI), while maintaining a sufficiently artifact-free image around the screw that the image characteristics of the surrounding tissue are still determinable.

27 Claims, 4 Drawing Sheets

(51) Int. Cl.
*A61B 90/00* (2016.01)
*A61L 31/18* (2006.01)
*A61L 31/02* (2006.01)
*A61B 17/00* (2006.01)

(52) U.S. Cl.
CPC ............ *A61B 90/39* (2016.02); *A61L 31/022* (2013.01); *A61L 31/128* (2013.01); *A61L 31/18* (2013.01); *A61B 2017/00526* (2013.01); *A61B 2017/00964* (2013.01); *A61B 2090/3966* (2016.02); *A61B 2090/3991* (2016.02)

(56) References Cited

U.S. PATENT DOCUMENTS

| | | | |
|---|---|---|---|
| 4,058,581 A | 11/1977 | Park | |
| 4,220,187 A | 9/1980 | Holmes | |
| 4,623,290 A * | 11/1986 | Kikuzawa | B29C 70/22 411/350 |
| 4,667,664 A | 5/1987 | Taylor et al. | |
| 4,706,659 A | 11/1987 | Matthews et al. | |
| 4,718,801 A | 1/1988 | Berecz | |
| 4,743,257 A | 5/1988 | Tormala et al. | |
| 4,750,905 A | 6/1988 | Koeneman et al. | |
| 4,824,314 A | 4/1989 | Stencel | |
| 4,863,330 A * | 9/1989 | Olez | B29C 70/081 411/424 |
| 4,875,474 A | 10/1989 | Border | |
| 4,909,690 A * | 3/1990 | Gapp | B29C 70/202 411/411 |
| 4,978,360 A | 12/1990 | Devanathan | |
| 4,988,350 A | 1/1991 | Herzberg | |
| 5,009,664 A | 4/1991 | Sievers | |
| 5,032,125 A | 7/1991 | Durham et al. | |
| 5,041,113 A | 8/1991 | Biedermann et al. | |
| 5,060,635 A | 10/1991 | Steur et al. | |
| 5,064,439 A | 11/1991 | Chang et al. | |
| 5,098,240 A * | 3/1992 | Gapp | B29C 70/202 411/424 |
| 5,181,930 A | 1/1993 | Dumbleton et al. | |
| 5,192,330 A | 3/1993 | Chang et al. | |
| 5,197,966 A | 3/1993 | Sommerkamp | |
| 5,292,215 A | 3/1994 | Roberts, III | |
| 5,320,100 A | 6/1994 | Herweck et al. | |
| 5,348,026 A | 9/1994 | Davidson | |
| 5,397,358 A | 3/1995 | Wenner et al. | |
| 5,437,526 A | 8/1995 | Herbst et al. | |
| 5,498,265 A | 3/1996 | Asnis | |
| 5,522,817 A | 6/1996 | Sander et al. | |
| 5,795,116 A | 8/1998 | Frank et al. | |
| 5,824,079 A | 10/1998 | Siegler et al. | |
| 5,879,352 A | 3/1999 | Filoso et al. | |
| 5,961,524 A | 10/1999 | Crombie | |
| 6,030,389 A | 2/2000 | Wagner et al. | |
| 6,077,880 A * | 6/2000 | Castillo | A61L 29/041 523/105 |
| 6,206,881 B1 | 3/2001 | Frigg et al. | |
| 6,306,140 B1 | 10/2001 | Siddiqui | |
| 6,342,055 B1 | 1/2002 | Eisermann et al. | |
| 6,471,707 B1 | 10/2002 | Miller et al. | |
| 6,605,090 B1 | 8/2003 | Trieu et al. | |
| 6,692,497 B1 | 2/2004 | Tormala et al. | |
| 6,692,498 B1 | 2/2004 | Niiranen et al. | |
| 6,730,091 B1 | 5/2004 | Pfefferle et al. | |
| 6,916,321 B2 | 7/2005 | TenHuisen et al. | |
| 6,921,402 B2 | 7/2005 | Contiliano et al. | |
| 7,419,714 B1 | 9/2008 | Magerl et al. | |
| 7,763,023 B2 | 7/2010 | Gotfried | |
| 7,785,325 B1 | 8/2010 | Milbank | |
| 7,850,690 B2 | 12/2010 | Frigg et al. | |
| 7,896,599 B2 | 3/2011 | Stephen et al. | |
| 7,914,244 B2 | 3/2011 | Bubulka et al. | |
| 8,080,043 B2 * | 12/2011 | Tormala | A61B 17/80 442/401 |
| 8,128,627 B2 | 3/2012 | Justin et al. | |
| 8,323,321 B2 | 12/2012 | Gradl | |
| 8,709,055 B2 * | 4/2014 | Beyar | A61B 17/1631 606/301 |
| 8,915,917 B2 | 12/2014 | Doherty et al. | |
| 9,358,056 B2 | 6/2016 | Stalcup et al. | |
| 10,154,867 B2 * | 12/2018 | Globerman | A61B 17/866 |
| 2002/0029043 A1 | 3/2002 | Ahrens et al. | |
| 2002/0133172 A1 | 9/2002 | Lambrecht et al. | |
| 2002/0156473 A1 | 10/2002 | Bramlet et al. | |
| 2003/0057590 A1 | 3/2003 | Loher et al. | |
| 2003/0153981 A1 | 8/2003 | Wang et al. | |
| 2003/0158555 A1 | 8/2003 | Sanders et al. | |
| 2004/0071954 A1 | 4/2004 | Hiraide et al. | |
| 2004/0073218 A1 | 4/2004 | Dahners | |
| 2004/0158252 A1 | 8/2004 | Prager et al. | |
| 2004/0260291 A1 | 12/2004 | Jensen | |
| 2005/0096656 A1 | 5/2005 | Behrens | |
| 2005/0131413 A1 | 6/2005 | O'Driscoll et al. | |
| 2005/0152770 A1 | 7/2005 | Tschakaloff et al. | |
| 2005/0161120 A1 | 7/2005 | Inagaki et al. | |
| 2005/0177153 A1 | 8/2005 | Guzman et al. | |
| 2005/0192578 A1 | 9/2005 | Horst | |
| 2005/0234457 A1 | 10/2005 | James et al. | |
| 2006/0004431 A1 | 1/2006 | Fuller et al. | |
| 2006/0009771 A1 | 1/2006 | Orbay et al. | |
| 2006/0015110 A1 | 1/2006 | Pepper | |
| 2006/0041261 A1 | 2/2006 | Osypka | |
| 2006/0079900 A1 | 4/2006 | Mathieu et al. | |
| 2006/0106390 A1 | 5/2006 | Jensen et al. | |
| 2006/0106400 A1 | 5/2006 | Fernandez et al. | |
| 2006/0116678 A1 | 6/2006 | Impellizzeri | |
| 2006/0149264 A1 | 7/2006 | Castaneda et al. | |
| 2006/0189996 A1 | 8/2006 | Orbay et al. | |
| 2006/0195085 A1 | 8/2006 | Happonen et al. | |
| 2006/0200142 A1 | 9/2006 | Sohngen et al. | |
| 2006/0235400 A1 | 10/2006 | Schneider | |
| 2006/0259039 A1 | 11/2006 | Pitkanen et al. | |
| 2006/0264948 A1 | 11/2006 | Williams | |
| 2006/0282168 A1 | 12/2006 | Sherman et al. | |
| 2007/0083207 A1 | 4/2007 | Ziolo et al. | |
| 2007/0110544 A1 | 5/2007 | Friedrich et al. | |
| 2007/0123878 A1 | 5/2007 | Shaver | |
| 2007/0162018 A1 | 7/2007 | Jensen et al. | |
| 2007/0167953 A1 | 7/2007 | Prien et al. | |
| 2007/0173843 A1 | 7/2007 | Matityahu | |
| 2007/0233105 A1 | 10/2007 | Nelson et al. | |
| 2007/0260244 A1 | 11/2007 | Wolter | |
| 2008/0046091 A1 | 2/2008 | Weiss et al. | |
| 2008/0140130 A1 | 6/2008 | Chan et al. | |
| 2008/0195157 A1 | 8/2008 | Orschler et al. | |
| 2008/0208259 A1 | 8/2008 | Gilbert et al. | |
| 2008/0234752 A1 | 9/2008 | Dahners | |
| 2008/0234762 A1 | 9/2008 | Forstein et al. | |
| 2008/0287951 A1 | 11/2008 | Stoneburner et al. | |
| 2008/0294201 A1 | 11/2008 | Huddleston, III | |
| 2009/0018588 A1 | 1/2009 | Eckhof et al. | |
| 2009/0043307 A1 | 2/2009 | Faccioli et al. | |
| 2009/0088807 A1 | 4/2009 | Castaneda et al. | |
| 2009/0228008 A1 | 9/2009 | Justin et al. | |
| 2009/0228048 A1 | 9/2009 | Duncan et al. | |
| 2009/0248089 A1 | 10/2009 | Jacofsky et al. | |
| 2009/0312803 A1 | 12/2009 | Austin et al. | |
| 2009/0326534 A1 | 12/2009 | Yamazaki et al. | |
| 2010/0016858 A1 | 1/2010 | Michel | |
| 2010/0042167 A1 | 2/2010 | Nebosky et al. | |
| 2010/0042215 A1 | 2/2010 | Stalcup et al. | |
| 2010/0094423 A1 | 4/2010 | Foley et al. | |
| 2010/0100134 A1 | 4/2010 | Mocanu | |
| 2010/0190138 A1 | 7/2010 | Giorno | |
| 2010/0217333 A1 | 8/2010 | McShane et al. | |
| 2010/0234847 A1 | 9/2010 | Impellizzeri | |
| 2010/0312286 A1 | 12/2010 | Dell'Oca | |
| 2010/0331842 A1 | 12/2010 | Milbank | |
| 2011/0015682 A1 | 1/2011 | Lewis et al. | |
| 2011/0106086 A1 | 5/2011 | Laird | |
| 2011/0218570 A1 | 9/2011 | Felix et al. | |
| 2011/0224737 A1 | 9/2011 | Lewis et al. | |
| 2011/0282395 A1 | 11/2011 | Beyar et al. | |
| 2011/0288598 A1 | 11/2011 | Moed et al. | |

(56) References Cited

U.S. PATENT DOCUMENTS

| | | | |
|---|---|---|---|
| 2011/0295319 | A1 | 12/2011 | Duplessis et al. |
| 2012/0029577 | A1 | 2/2012 | Kerr et al. |
| 2012/0059376 | A1* | 3/2012 | Rains .............. A61B 17/72 606/62 |
| 2012/0065638 | A1 | 3/2012 | Moore |
| 2012/0083847 | A1 | 4/2012 | Huebner et al. |
| 2012/0136396 | A1 | 5/2012 | Baker et al. |
| 2012/0203285 | A1 | 8/2012 | Rotini et al. |
| 2012/0283790 | A1 | 11/2012 | Meyer, III |
| 2012/0330361 | A1 | 12/2012 | Gepstein |
| 2013/0079829 | A1 | 3/2013 | Globerman et al. |
| 2013/0116693 | A1 | 5/2013 | Nelson et al. |
| 2013/0184765 | A1 | 7/2013 | Beyar et al. |
| 2013/0218214 | A1 | 8/2013 | Beyar et al. |
| 2013/0237813 | A1 | 9/2013 | Beyar et al. |
| 2013/0261675 | A1 | 10/2013 | Fritzinger |
| 2013/0296863 | A1 | 11/2013 | Globerman et al. |
| 2013/0296952 | A1 | 11/2013 | Globerman et al. |
| 2013/0315689 | A1* | 11/2013 | Jeong .............. B29C 70/083 411/424 |
| 2013/0325007 | A1 | 12/2013 | Beyar et al. |
| 2014/0222001 | A1 | 8/2014 | Beyar et al. |
| 2015/0289911 | A1* | 10/2015 | Beyar .............. A61B 17/7059 606/70 |
| 2015/0297267 | A1* | 10/2015 | Gepstein .......... A61B 17/7023 606/264 |
| 2015/0327893 | A1 | 11/2015 | Beyar et al. |
| 2016/0038206 | A1 | 2/2016 | McDonnell |
| 2016/0067046 | A1 | 3/2016 | Globerman et al. |
| 2016/0113695 | A1 | 4/2016 | Globerman et al. |
| 2017/0156773 | A1* | 6/2017 | Beyar .............. A61B 17/866 |
| 2017/0312948 | A1 | 11/2017 | Sodore et al. |
| 2018/0236736 | A1* | 8/2018 | Burgess .......... A61L 27/28 |
| 2018/0256231 | A1 | 9/2018 | Globerman et al. |

FOREIGN PATENT DOCUMENTS

| | | |
|---|---|---|
| CN | 1367669 | 9/2002 |
| CN | 1482890 | 3/2004 |
| CN | 1486162 | 3/2004 |
| CN | 1586416 | 3/2005 |
| CN | 1694653 | 11/2005 |
| CN | 2746884 | 12/2005 |
| CN | 1819799 | 8/2006 |
| CN | 2801080 | 8/2006 |
| CN | 1845711 | 10/2006 |
| CN | 101304695 | 11/2008 |
| CN | 101340851 | 1/2009 |
| CN | 101426444 | 5/2009 |
| CN | 101500499 | 8/2009 |
| DE | 4343117 | 6/1995 |
| EP | 0551574 | 7/1993 |
| EP | 0979637 | 2/2000 |
| EP | 1042989 | 10/2000 |
| EP | 1101459 | 5/2001 |
| EP | 1598028 | 11/2005 |
| EP | 1733704 | 12/2006 |
| EP | 1779796 | 5/2007 |
| EP | 1857066 | 11/2007 |
| EP | 2198792 | 6/2010 |
| EP | 2292176 | 3/2011 |
| FR | 2555902 | 6/1985 |
| FR | 2646767 | 11/1990 |
| FR | 2829378 | 3/2003 |
| GB | 2442706 | 4/2008 |
| JP | 02-198550 | 8/1990 |
| JP | 05-000157 | 1/1993 |
| JP | 05-092019 | 4/1993 |
| JP | 06-500945 | 2/1994 |
| JP | 2000-116664 | 4/2000 |
| JP | 2002-536048 | 10/2002 |
| JP | 2004-097794 | 4/2004 |
| JP | 2005-329244 | 12/2005 |
| JP | 2007-021001 | 2/2007 |
| JP | 2007-125387 | 5/2007 |
| JP | 2008-036094 | 2/2008 |
| SU | 1111748 | 9/1984 |
| WO | WO 92/18068 | 10/1992 |
| WO | WO 93/13713 | 7/1993 |
| WO | WO 94/07425 | 4/1994 |
| WO | WO 96/02203 | 2/1996 |
| WO | WO 96/09014 | 3/1996 |
| WO | WO 96/19336 | 6/1996 |
| WO | WO 01/15637 | 3/2001 |
| WO | WO 2006/090226 | 8/2006 |
| WO | WO 2007/009123 | 1/2007 |
| WO | WO 2007/010671 | 1/2007 |
| WO | WO 2007/035772 | 3/2007 |
| WO | WO 2008/033742 | 3/2008 |
| WO | WO 2008/064346 | 5/2008 |
| WO | WO 2008/092192 | 8/2008 |
| WO | WO 2009/002890 | 12/2008 |
| WO | WO 2009/143374 | 11/2009 |
| WO | WO 2009/152270 | 12/2009 |
| WO | WO 2009/152272 | 12/2009 |
| WO | WO 2010/045473 | 4/2010 |
| WO | WO 2010/082183 | 7/2010 |
| WO | WO 2011/042407 | 4/2011 |
| WO | WO 2011/154891 | 12/2011 |
| WO | WO 2012/107913 | 8/2012 |

OTHER PUBLICATIONS

Notice of Reason for Rejection dated May 27, 2016 From the Japanese Patent Office Re. Application No. 2015-133386 and Its Translation Into English.
Notice of Allowance dated Sep. 25, 2018 From the US Patent and Trademark Office Re. U.S. Appl. No. 14/757,524. (100 pages).
Notification of Office Action and Search Report dated Jul. 7, 2016 From the State Intellectual Property Office of the People's Republic of China Re. Application No. 201410413164.7 and Its Translation Into English.
Official Action dated May 15, 2017 From the US Patent and Trademark Office Re. U.S. Appl. No. 14/811,859. (20 pages).
Applicant-Initiated Interview Summary dated Aug. 12, 2016 From the US Patent and Trademark Office Re. U.S. Appl. No. 13/742,462.
Notification of Office Action and Search Report dated Aug. 11, 2016 From the State Intellectual Property Office of the People's Republic of China Re. Application No. 201410413073.3 and Its Translation Into English.
Restriction Official Action dated Jun. 5, 2018 From the US Patent and Trademark Office Re. U.S Appl. No. 14/757,524. (7 pages).
Notice of Reason for Rejection dated Dec. 27, 2016 From the Japanese Patent Office Re. Application No. 2015-133386 and Its Machine Translation Into English.
Communication Pursuant to Article 94(3) EPC dated Jun. 6, 2017 From the European Patent Office Re. Application No. 11731110.0. (6 Pages).
Corrected Notification of Office Action and Search Report dated Nov. 17, 2017 From the State Intellectual Property Office of the People's Republic of China Re. Application No. 201510441068.8 and Its Translation Into English. (20 Pages).
Notification of Office Action and Search Report dated Apr. 6, 2017 From the State Intellectual Property Office of the People's Republic of China Re. Application No. 201510441074.3 and Its Translation Into English. (19 Pages).
Notification of Office Action dated Jan. 19, 2017 From the State Intellectual Property Office of the People's Republic of China Re. Application No. 201410413164.7. (3 Pages).
Official Action dated Oct. 14, 2016 From the US Patent and Trademark Office Re. U.S. Appl. No. 13/742,462.
Official Action dated Dec. 19, 2016 From the US Patent and Trademark Office Re. U.S. Appl. No. 14/945,545. (83 pages).
Official Action dated Dec. 21, 2016 From the US Patent and Trademark Office Re. U.S. Appl. No. 14/811,859. (67 pages).
European Search Report and the European Search Opinion dated Nov. 8, 2017 From the European Patent Office Re. Application No. 17179078.5. (9 Pages).

(56) References Cited

OTHER PUBLICATIONS

Notification of Office Action and Search Report dated Nov. 17, 2017 From the State Intellectual Property Office of the People's Republic of China Re. Application No. 20151044106.8. (9 Pages).
Applicant-Initiated Interview Summary dated Oct. 30, 2017 From the US Patent and Trademark Office Re. U.S. Appl. No. 14/811,859. (3 pages).
Official Action dated Mar. 31, 2017 From the US Patent and Trademark Office Re. U.S. Appl. No. 14/945,545. (16 Pages).
Translation of Notification of Office Action dated Jan. 19, 2017 From the State Intellectual Property Office of the People's Republic of China Re. Application No. 201410413164.7. (4 Pages).
Advisory Action Before the Filing of an Appeal Brief dated May 9, 2016 From the US Patent and Trademark Office Re. U.S. Appl. No. 13/985,048.
Advisory Action Before the Filing of an Appeal Brief dated Jun. 29, 2015 From the US Patent and Trademark Office Re. U.S. Appl. No. 13/702,334.
Applicant-Initiated Interview Summary dated Jun. 9, 2015 From the US Patent and Trademark Office Re. U.S. Appl. No. 13/702,334.
Applicant-Initiated Interview Summary dated Oct. 8, 2014 From the US Patent and Trademark Office Re. U.S. Appl. No. 13/935,501.
Applicant-Initiated Interview Summary dated Jan. 12, 2016 From the US Patent and Trademark Office Re. U.S. Appl. No. 13/852,100.
Applicant-Initiated Interview Summary dated Oct. 17, 2013 From the US Patent and Trademark Office Re. U.S. Appl. No. 13/144,938.
Applicant-Initiated Interview Summary dated Oct. 19, 2015 From the US Patent and Trademark Office Re. U.S. Appl. No. 13,742,462.
Applicant-Initiated Interview Summary dated Nov. 21, 2014 From the US Patent and Trademark Office Re. U.S. Appl. No. 13/935,497.
Applicant-Initiated Interview Summary dated Dec. 22, 2015 From the US Patent and Trademark Office Re. U.S. Appl. No. 13/702,334.
Communication Pursuant to Article 94(3) EPC dated Feb. 2, 2016 From the European Patent Office Re. Application No. 13151490.3.
Communication Pursuant to Article 94(3) EPC dated Jul. 2, 2013 From the European Patent Office Re. Application No. 10702750.0.
Communication Pursuant to Article 94(3) EPC dated Jul. 11, 2014 From the European Patent Office Re. Application No. 13151490.3.
Communication Pursuant to Article 94(3) EPC dated Nov. 19, 2014 From the European Patent Office Re. Application No. 10702750.0.
Communication Pursuant to Article 94(3) EPC dated Apr. 29, 2015 From the European Patent Office Re. Application No. 13151490.3.
Communication Pursuant to Rules 70(2) and 70a(2) EPC and Reference to Rule 39(1) EPC dated Jul. 22, 2013 From the European Patent Office Re. Application No. 13151490.3.
Communication Relating to the Results of the Partial International Search dated May 17, 2010 From the International Searching Authority Re.: Application No. PCT/IB2010/050225.
Communication Relating to the Results of the Partial International Search dated May 29, 2012 From the International Searching Authority Re. Application No. PCT/IB2012/050645.
Communication Relating to the Results of the Partial International Search dated Sep. 29, 2011 From the International Searching Authority Re. Application No. PCT/IB2011/052468.
Communication Under Rule 71(3) EPC dated Jul. 15, 2015 From the European Patent Office Re. Application No. 10702750.0.
Corrected Notice of Allowability dated Feb. 11, 2014 From the US Patent and Trademark Office Re. U.S. Appl. No. 13/144,938.
Corrected Notice of Allowability dated Feb. 14, 2014 From the US Patent and Trademark Office Re. U.S. Appl. No. 13/144,938.
European Search Report and the Written Opinion dated Apr. 18, 2013 From the European Patent Office Re. Application No. 13151490.3.
International Preliminary Report on Patentability dated Dec. 20, 2012 From the International Bureau of WIPO Re. Application No. PCT/IB2011/052468.
International Preliminary Report on Patentability dated Aug. 22, 2013 From the International Bureau of WIPO Re. Application No. PCT/IB2012/050645.
International Preliminary Report on Patentability dated Jul. 28, 2011 From the International Bureau of WIPO Re. Application No. PCT/IB2010/050225.
International Search Report and the Written Opinion dated Nov. 10, 2010 From the International Searching Authority Re. Application No. PCT/IB2010/050225.
International Search Report and the Written Opinion dated Aug. 24, 2012 From the International Searching Authority Re: Application No. PCT/IB2012/050645.
International Search Report and the Written Opinion dated Dec. 29, 2011 From the International Searching Authority Re. Application No. PCT/IB2011/052468.
Notice of Allowance dated Apr. 2, 2015 From the US Patent and Trademark Office Re. U.S. Appl. No. 13/935,497.
Notice of Allowance dated Apr. 3, 2015 From the US Patent and Trademark Office Re. U.S. Appl. No. 14/246,161.
Notice of Allowance dated Dec. 11, 2013 From the US Patent and Trademark Office Re. U.S. Appl. No. 13/144,938.
Notice of Allowance dated Feb. 22, 2016 From the US Patent and Trademark Office Re. U.S. Appl. No. 13/702,334.
Notice of Reason for Rejection dated Jun. 3, 2014 From the Japanese Patent Office Re. Application No. 2011-545832 and Its Translation Into English.
Notice of Reason for Rejection dated Nov. 15, 2013 From the Japanese Patent Office Re. Application No. 2011-545832 and Its Translation Into English.
Notification of Office Action and Search Report dated Dec. 2, 2015 From the State Intellectual Property Office of the People's Republic of China Re. Application No. 201410413164.7.
Notification of Office Action and Search Report dated Jan. 13, 2016 From the State Intellectual Property Office of the People's Republic of China Re. Application No. 201410412613.6.
Notification of Office Action dated Mar. 7, 2014 From the State Intellectual Property Office of the People's Republic of China Re. Application No. 201080012276.1 and Its Translation Into English.
Notification of Office Action dated Oct. 18, 2013 From the State Intellectual Property Office of the People's Republic of China Re. Application No. 201080012276.1 and Its Translation Into English.
Notification of Office Action dated Dec. 28, 2015 From the State Intellectual Property Office of the People's Republic of China Re. Application No. 201410413073.3.
Notification of Office Action dated Oct. 29, 2014 From the State Intellectual Property Office of the People's Republic of China Re. Application No. 201180038951.2 and Its Translation Into English.
Office Action dated Apr. 2, 2014 From the Israel Patent Office Re. Application No. 214105 and Its Translation Into English.
Office Action dated Aug. 10, 2014 From the Israel Patent Office Re. Application No. 214105 and Its Translation Into English.
Office Action dated Jan. 22, 2015 From the Israel Patent Office Re. Application No. 223485.
Official Action dated Apr. 1, 2015 From the US Patent and Trademark Office Re. U.S. Appl. No. 13/935,501.
Official Action dated Feb. 1, 2016 From the US Patent and Trademark Office Re. U.S. Appl. No. 13/852,145.
Official Action dated Mar. 2, 2016 From the US Patent and Trademark Office Re. U.S. Appl. No. 13/852,100.
Official Action dated Aug. 5, 2014 From the US Patent and Trademark Office Re. U.S. Appl. No. 13/935,497.
Official Action dated Nov. 10, 2014 From the US Patent and Trademark Office Re. U.S. Appl. No. 13/702,334.
Official Action dated Jul. 11, 2014 From the US Patent and Trademark Office Re. U.S. Appl. No. 13/935,501.
Official Action dated Jun. 12, 2015 From the US Patent and Trademark Office Re. U.S. Appl. No. 13/742,462.
Official Action dated Jul. 17, 2014 From the US Patent and Trademark Office Re. U.S. Appl. No. 14/246,161.
Official Action dated Mar. 17, 2015 From the US Patent and Trademark Office Re. U.S. Appl. No. 13/702,334.
Official Action dated Mar. 17, 2016 From the US Patent and Trademark Office Re. U.S. Appl. No. 13/742,462.
Official Action dated Dec. 19, 2014 From the US Patent and Trademark Office Re. U.S. Appl. No. 13/742,462.

(56) References Cited

OTHER PUBLICATIONS

Official Action dated Dec. 19, 2014 From the US Patent and Trademark Office Re. U.S. Appl. No. 13/935,497.
Official Action dated Aug. 21, 2015 From the US Patent and Trademark Office Re. U.S. Appl. No. 13/702,334.
Official Action dated Jan. 22, 2015 From the US Patent and Trademark Office Re. U.S. Appl. No. 14/246,161.
Official Action dated Dec. 23, 2014 From the US Patent and Trademark Office Re. U.S. Appl. No. 13/935,501.
Official Action dated Jan. 27, 2014 From the US Patent and Trademark Office Re. U.S. Appl. No. 13/935,501.
Official Action dated Jun. 27, 2013 From the US Patent and Trademark Office Re. U.S. Appl. No. 13/144,938.
Official Action dated Sep. 28, 2015 From the US Patent and Trademark Office Re. U.S. Appl. No. 13/852,100.
Official Action dated Apr. 29, 2015 From the US Patent and Trademark Office Re. U.S. Appl. No. 13/985,048.
Official Action dated Jan. 29, 2016 From the US Patent and Trademark Office Re. U.S. Appl. No. 13/985,048.
Official Decision of Rejection dated Mar. 3, 2015 From the Japanese Patent Office Re. Application No. 2011-545832 and Its Translation Into English.
Requisition by the Examiner and Examination Search Report dated Mar. 17, 2015 From the Canadian Intellectual Property Office Re. Application No. 2,749,684.
Restriction Official Action dated Aug. 1, 2014 From the US Patent and Trademark Office Re. U.S. Appl. No. 13/742,462.
Restriction Official Action dated Mar. 22, 2013 From the US Patent and Trademark Office Re. U.S. Appl. No. 13/144,938.
Restriction Official Action dated Jun. 25, 2015 From the US Patent and Trademark Office Re. U.S. Appl. No. 13/852,100.
Restriction Official Action dated May 30, 2014 From the US Patent and Trademark Office Re. U.S. Appl. No. 14/246,161.
Search Report dated Oct. 29, 2014 From the State Intellectual Property Office of the People's Republic of China Re. Application No. 201180038951.2 and Its Translation Into English.
Translation Dated Feb. 9, 2015 of Office Action dated Jan. 22, 2015 From the Israel Patent Office Re. Application No. 223485.
Translation Dated Jan. 17, 2016 of Notification of Office Action dated Dec. 28, 2015 From the State Intellectual Property Office of the People's Republic of China Re. Application No. 201410413073.3.
Translation Dated Dec. 20, 2015 of Notification of Office Action and Search Report dated Dec. 2, 2015 From the State Intellectual Property Office of the People's Republic of China Re. Application No. 201410413164.7.
Translation Dated Jan. 27, 2016 of Notification of Office Action dated Jan. 13, 2016 From the State Intellectual Property Office of the People's Republic of China Re. Application No. 201410412613.6.
Translation of Notification of Office Action dated Apr. 12, 2013 From the State Intellectual Property Office of the People's Republic of China Re. Application No. 201080012276.1.
Translation of Search Report dated Apr. 12, 2013 From the State Intellectual Property Office of the People's Republic of China Re. Application No. 201080012276.1.
Translation of Search Report dated Oct. 18, 2013 From the State Intellectual Property Office of the People's Republic of China Re. Application No. 201080012276.1.
Official Action dated Nov. 3, 2016 From the US Patent and Trademark Office Re. U.S. Appl. No. 13/852,145.

* cited by examiner

MULTI-LAYER COMPOSITE MATERIAL BONE SCREW

RELATED APPLICATION

This application is related to co-filed, co-pending and co-assigned U.S. patent application Ser. No. 14/757,524 entitled "MULTI-LAYER COMPOSITE MATERIAL BONE SCREW" by Oren GLOBERMAN, Mordechay BEYAR and Hila WACHSLER-AVRAHAMI, the disclosure of which is incorporated herein by reference.

FIELD AND BACKGROUND OF THE INVENTION

The present invention, in some embodiments thereof, relates to composite material bone implant devices—mainly, but not limited to, screw constructs for such devices; and more particularly, but not exclusively, to such devices as applied to implant devices constructed of fiber-reinforced polymer matrices.

Bone implant screws (bone screws) are used to secure and stabilize bone implants, for example, by attachment through an aperture of a bone implant into bone, and/or by attaching other bone implant parts to each other. Examples include spine implant systems comprising pedicle screws and rods.

Normally, bone screws are made of metal, for example, titanium and/or titanium alloy. Although metallic implants provide numerous advantages, the metals potentially obstruct visualization of the implant and surrounding tissue upon using fluoroscopy, CT and/or MR imaging. Such imaging means are important for follow-up evaluation, including for identification of exact screw location, and/or status of tissue (for example, bone, nerve tissue, and/or potentially cancerous tissue) surrounding the bone implant and/or bone screw. Furthermore, metallic implants interfere with radiotherapy given to oncology patients. The relatively large electronic mass and the scattering phenomena reduce the radiation effectiveness and necessitate radiation in higher doses that further provoke side effects on surrounding tissue.

Metal construction normally provides adequate bending and torsion strength to resist implant fracture. However, the rigid metal implant, having different elasticity than that of the bone, may contribute to stress shielding leading, for example, to bone loss. Metals such as stainless steel may cause biocompatibility problems related to corrosion and sensitization reactions (mainly due to allergy to nickel). Resistance of metals to fatigue loads is potentially poorer than a resistance of some composite materials to a similar fatigue load.

Non-metal, composite material, bone implants are currently available on the market; for example, cage and vertebral body replacement devices made of carbon-polyether ether ketone (PEEK). Lumbar and/or cervical cages are also produced from PEEK, carbon fiber reinforced polymer or carbon. Carbon fiber-reinforced PEEK, are also used for other bone applications, such as intramedullary nails and bone plates (CarboFix Orthopedics Ltd.).

SUMMARY OF THE INVENTION

There is provided, in accordance with some exemplary embodiments, a fiber-reinforced composite material bone screw comprising: a screw core comprising fiber-reinforced polymer matrix, the screw having a threaded region along a shaft defined by the screw core; and a layer comprising particles of powdered radiopaque marker material distributed within a polymer matrix, the layer arranged circumferentially around at least a portion of the threaded region, and beneath the threaded surface.

According to some embodiments, the radiopaque marker material comprises at least one from the group consisting of gold, platinum, rhenium, tungsten, tantalum, barium sulfate, and/or iodinated compounds.

According to some embodiments, the radiopaque marker material is in a powdered form, the particles of the powder being less than 200 µm in diameter.

According to some embodiments, the layer comprising radiopaque marker material is at least 10 µm from the outer surface of the screw core.

According to some embodiments, the layer comprising radiopaque marker material extends circumferentially around at least 70% of the circumference of the portion of the screw core.

According to some embodiments, the layer comprising radiopaque marker material extends circumferentially entirely around the circumference of the portion of the screw core.

According to some embodiments, the bone screw comprises a metallic outer layer circumferentially surrounding the layer comprising particles of radiopaque material.

According to some embodiments, the material of the metallic outer layer comprises at least one of the group comprising titanium and titanium alloy.

According to some embodiments, an inner portion of the metallic outer layer comprises the radiopaque marker material in a sheet form.

According to some embodiments, the layer comprising radiopaque marker material comprises a material having a greater linear attenuation coefficient than the outer material of the metallic outer layer.

According to some embodiments, the radiopaque marker material is concentrated along at least one path following a winding pitch of the thread of the threaded shaft.

According to some embodiments, the layer comprising radiopaque marker material comprises at least one radiopaque region at a screw tip at one end of a longitudinal axis of the bone screw.

There is provided, in accordance with some exemplary embodiments, a fiber-reinforced composite material bone screw comprising: a screw core comprising fiber-reinforced polymer matrix composite material; and a thread region circumferentially surrounding the screw core at least along a threaded shaft of the screw core, the thread region also comprising fiber-reinforced polymer matrix composite material, and radially extending between the thread valley and the thread peak; wherein the fibers of the fiber-reinforced polymer matrix composite material of the thread region comprise at leak a first fiber population and a second fiber population, wherein at least 10% of the fibers of the first population pass at an angle of at least 10 degrees relative to fibers of the second fiber population; the at least first and second populations interspersed with each other and within the polymer matrix. According to some embodiments, the fibers of the thread region also alternately extend radially inward and outward.

According to some embodiments, the thread region is formed by compression molding.

According to some embodiments, the fibers of the thread region comprise a substantially continuous distribution of orientations relative to a thread pitch of the screw, with no gaps of missing orientations wider than about 5°.

According to some embodiments, the fibers of the thread region comprise a substantially continuous distribution of orientations relative to a thread pitch of the screw through all angles tangential to the screw core.

According to some embodiments, the fibers of the thread region comprise a substantially continuous distribution of orientations relative to a thread pitch of the screw through all angles.

According to some embodiments, all fiber orientations within the thread region s are about equally represented.

According to some embodiments, fibers extending through the thread region also extend through a thread base region comprised of the composite material extending continuously between the thread windings.

According to some embodiments, fibers of the thread region are randomly dispersed at various directions with respect to a winding direction of the thread. According to some embodiments, fibers of the thread region comprise a population of fiber lengths passing within the thread region which is substantially omnidirectional at least circumferentially with respect to a thread pitch of the thread region.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
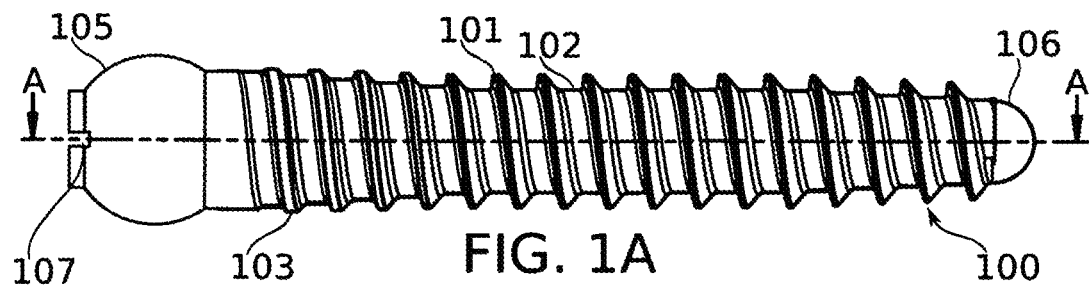
FIGS. 1A-1B schematically illustrate in profile (FIG. 1A) and in cross-section (FIG. 1B) a composite construction bone screw having a layered construction, according to some exemplary embodiments of the invention.

The present invention, in some embodiments thereof, relates to composite material bone implant devices—mainly, but not limited to, screw constructs for such devices; and more particularly, but not exclusively, to such devices as applied to implant devices constructed of fiber-reinforced polymer matrices.

Overview

A broad aspect of some embodiments of the current invention relates to the layered structure of a composite material body bone screw, optionally with a metallic outer surfacing layer.

In some embodiments, at least a threaded portion of a bone screw shaft comprises a metallic layer providing an outer surface of the bone screw. The layer coats and/or is formed against an inner screw body of differing construction. For example, the body is of composite fiber construction, for example, carbon fiber-reinforced polyether ether ketone (CFR-PEEK). Use of a composite fiber constructed body potentially provides advantages (compared to an equivalent all-metal body) such as, for example, reduced stress shielding and lower imaging artifact incidence, optionally with strength that is about as high as all-metal equivalent. Combined with a composite fiber-reinforced matrix screw body, a metal outer surface provides a potential advantage for toughening the surface against wear.

In some embodiments, the metallic outer surface layer comprises titanium, for example, pure titanium (Ti) and/or a titanium alloy such as Ti-6Al-4V, and/or another metal. The metal is optionally shaped, for example, as a foil, coating, tube, and/or shell. In some embodiments, the thickness of the metallic outer surface layer is, for example, between 1 µm and 200 µm. Optionally, the thickness is, for example, between 4-5 µm, 10-50 µm, 2-9 µm, 70-90 µm, 20-60 µm, 90-120 µm, 100-150 µm, or within another range of thicknesses having the same, greater, lesser, and/or intermediate bounds. Optionally, the thickness is chosen to be thin enough to significantly prevent artifacts in imaging (radioimaging in particular); for example, to prevent at least 50%, 70%, 90%, 95%, intermediate, or greater percentages of artifact strength and/or extent as compared to artifacts generated (for example, in MRI or CT imaging) if the whole screw were formed of pure titanium. With respect to imaging artifact reduction, it is also noted that titanium, compared to many metals used in biocompatible applications, provides a potential advantage in terms of its high strength/toughness in relation to its linear attenuation coefficient (an index of radiopacity).

An aspect of some embodiments of the current invention relates to radiopacity added to an otherwise substantially radiolucent bone screw (for example, a bone screw coated with a layer of titanium thin enough to be radiolucent as described herein). In some embodiments, the radiolucency of a metal coated bone screw is too high in some conditions and/or imaging energies. Simply thickening the outer coating is potentially insufficient to overcome this, and/or inconvenient for manufacturing.

In some embodiments, radiopacity is added to a relatively radiolucent bone screw with a metallic layer by use of a particularly radiopaque material, for example, gold, platinum, rhenium, tungsten, tantalum, barium sulfate, and/or iodinated compounds. This potentially allows a relatively small amount of material to be used to achieve a comparatively greater radiopacity. Potentially, interference with other properties of the bone screw (mechanical strength, in particular), is reduced by this choice of materials for lending radiopacity to a screw.

The distribution of radiopaque material is optionally to all or a part of the inner surface of the composite bone screw's outer layer. Optionally, the radiopaque material is provided within a layer of the composite bone screw which is near or at the outer surface of the bone screw. In some embodiments, the radiopaque material is within the outer surface of the bone screw by at least, for example, 10 µm, 20 µm, 30 µm, 50 µm, 100 µm, 150 µm, 200 µm, or another greater, lesser or intermediate distance from the outer surface. In some embodiments, a portion of the radiopaque material is distributed within thread bodies (raised portions of the thread windings) of the composite bone screw. In some embodiments, the radiopaque material is distributed partially or fully in a region underneath the thread bodies. In some embodiments, the layer comprising the radiopaque material circumferentially surrounds a portion of the core of the composite bone screw, for example, a threaded region of the bone screw shaft. In some embodiments, the layer extends over at least 70%, 80%, 90%, or 100% of the circumference a surrounded portion of the composite bone screw, for example, a threaded portion of the bone screw.

The radiopaque material is provided, for example, as a powder, grains, particles, foil, or in another form. In some embodiments, radiopaque material provided in particulate form comprises particles of a diameter less than, for example, 200 µm, 100 µm, 50 µm, 25 µm, 10 µm, or another larger, smaller, or intermediate size. Optionally, this diameter is a maximum diameter of the particle. In some embodiments, particles are distributed in a polymer matrix. Optionally, the polymer matrix material comprises material of the polymer matrix of the composite fiber-reinforced material. Optionally, the polymer matrix material comprises, for example, PEEK. A potential advantage of using particles of a radiometrically dense material (such as a high atomic weight metal) for providing radiopacity is to achieve a given level of radiopacity (and associated visualizability) with a lowered volume of material which could potentially interfere with the mechanical strength properties of the composite fiber-reinforced polymer matrix material in which it is embedded.

In some embodiments, the radiopaque layer increases the radiopacity of the screw portion (for example, a longitudinally defined region along the screw shaft) it occupies by at least 50%. Optionally, the increase in overall radiopacity is at least 60%, 80%, 90%, 100%, 200%, or another greater, smaller, or intermediate amount.

Optionally, the radiopaque part is localized to one or more of the major structural regions of the screw (shaft, tip, and/or head, for example). Optionally, the radiopaque part is sparsely distributed as distinct concentrations of material in a region of the screw, covering, for example, about 1%, 5%, 10%, or another greater, lesser, or intermediate fraction of the surface in the region. Optionally, the radiopaque material is distributed in a pattern which identifies a structural feature of the bone screw and/or a limit of its extent. For example, the radiopacity is positioned to outline the screw shaft or a portion thereof, to identify a limit of the screw tip or head, and/or to identify an axial and/or rotational orientation of the screw.

An aspect of some embodiments of the invention relates to use of layers having both thread-pitched and steeply-pitched composite fiber orientations.

In some embodiments, at least one layer (in particular, but not only, relatively upper layers) of a composite material-construction screw comprise pre-impregnated tape (prepreg) wound with fibers to an orientation which follows the pitch of the threads of the screw. This provides a potential advantage for strength to resist shearing forces during insertion/removal, and/or to reduce anisotropies in stresses due to fiber deformations introduced by the screw threads themselves. The screw pitch optionally is in a range, for example, of between 0.8 mm and 6 mm, and/or within another range having the same, longer, shorter, and/or intermediate bounds.

In some embodiments, other layers of the screw are pitched at ±45° angles relative to a longitudinal axis of the bone screw, or at other relatively steep angles, for example, angles offset to within ±30-60° of the longitudinal axis of the bone screw. Such layers offer a potential advantage for the resistance to torsion of the screw.

By a convention used herein, positive pitch/winding angle degrees (for example, +45°) denote winding which advances in the direction of the right hand rule, following the winding direction of standard screw threads. Negative degrees (for example, −45°) denotes the reverse winding direction.

An aspect of some embodiments of the invention relates to production of composite fiber layers in the thread of a composite material screw having relatively isotropic distributions of fibers. For example, fibers are distributed substantially non-directionally, non-directionally within a layer (for example, a layer of prepreg tape), multi-directionally (for example, in 3, 4, 5, 6, or more discrete directions), and/or are continuously distributed over a wide range of angles.

In some embodiments, the threads of a fiber-reinforced composite material screw are substantially shaped from a blank, for example, by a compression molding operation. Optionally, mold shaping of a blank is followed by a finishing step such as machining. In some embodiments, the thread region of a provided blank comprises one or more layers of matrix pre-impregnated composite fiber (pre-preg), optionally in the form of a tape or sheet. Optionally, the distribution of reinforcing fibers in the tape is broad with respect to orientation and/or fiber length. For example, the orientation of the reinforcing fibers is substantially uniform in all directions in the plane of the tape. In some embodiments, the distribution as a function of orientation angle (able to take on a value from 0° to 180°) is substantially continuous over a range of at least 45°, 60°, 90°, 135°, 180°, or another smaller or intermediate range of angles.

In some embodiments, an injectable fiber/matrix composite material is injected to a thread-shaping mold, such that substantially non-directional fiber orientations are obtained in the molded product.

A potential advantage of providing a screw thread with a wide range of fiber orientations is to provide strengthening against a wider range of force directions and distributions. Potentially, threads are a relatively delicate feature of a composite material screw, due to relatively small dimensions, a relatively exposed position at or near the surface, and/or a variable roles in bearing forces, for example, during installation operations such as screwing and/or unscrewing, and during a service life potentially exposed to torquing and bending.

Potentially, fibers oriented along the thread, for example, resist torques applied during screwing-unscrewing, but contribute little to resisting longitudinal and/or bending forces which might actually or in tendency act to strip the thread. For example, longitudinal force applied to the point of a thread could apply torque that concentrates (for example, at the thread base) and induces cracking.

However, fibers at other angles (for example, crossing the thread pitch) would tend to create more reinforcement for the thread to resist such longitudinal forces. Potentially, fibers that are near in angle to the thread (within 5°, 10°, 15°, or another larger or smaller relative orientation), but cross between two or more threads, would be effective in taking up strain that would otherwise be transferred to the relatively weak matrix by being relatively straight.

At least some more superficial fibers crossing the threads at more oblique angles are potentially also more "wavy" after molding (which could reduce their ability to shield the matrix from initial strain); having been deformed during shaping by flow entering the thread bodies, and/or flow leaving the valleys in between threads bodies. Nevertheless, such fibers potentially act as anchors to resist thread separation, and/or act as stops to prevent spreading of cracks which do form. In some embodiments, substantially anisotropic fiber orientation helps to ensure that there is no direction along which a microcrack can easily propagate to form a larger crack. Potentially, this helps to resist modes of thread separation such as chipping or longitudinal torquing.

An aspect of some embodiments of the invention relates to production of composite fiber layers having relatively straight and uniform populations of fibers for transferring stresses to fiber strain, together with a complex molded shape.

For longitudinally oriented composite fibers, a consideration for production of a high flex strength is keeping the fibers straight, so that a relatively small flexure rapidly produces stress distributed over a relatively large population of reinforcing fibers in a particular region. However, where compression molding includes axially directed forces, and/or significant flow of material to conform to a complex shape (for example, a thread), the result is potentially "wavy", folded, or otherwise non-straight reinforcing fibers.

In some embodiments, straight fiber orientation is maintained by molding a blank comprising straight fibers (for example, laid down by layering of prepreg tape having a population of such fibers within it) in conditions substantially lacking axially-directed compression forces and/or undulating flow. A second and/or subsequent molding step is then carried out so that axially-directed compression forces are directed away from the straight fibers into other material; and/or are controlled by sizing of the straight-fiber blank and/or a straight-fiber blank with added overlay, relative to the mold so that axial forces do not disturb the orientations of to the straight fibers. Direction of forces into other materials comprises, for example, making the blank harder (for example, by a pre-compression step and/or by control of softening), and/or ensuring that other layers are softer (for example, by choice of prepreg material, winding tightness and/or positioning of buffer material).

Optionally, a uniformly straight fiber orientation comprises a fiber which deviates from a straight line along its length with an amplitude less than 5 μm, 10 μm, 15 μm, 20 μm, or less than another greater, lesser, or intermediate value.

Optionally, a uniformly straight fiber orientation comprises a fiber with a total length within 1% of the longitudinal extent of the fiber. Optionally, the difference of the two lengths is less than 0.1%, 0.25%, 0.5%, 2%, or another greater, lesser, or intermediate difference.

For fibers passing through a region of screw thread, distortion potentially reaches several layers down into the body of the composite material bone screw. Deformations during compression molding can increase the vulnerability of the screw by reducing the ability of fibers to shield the matrix from strain. In some embodiments, initial winding is performed with extra material positioned underneath threads such that initially laid up layer fiber positions are near to where they will be after manufacturing is complete. Optionally, steeply angled layers are supplemented by windings angled with the thread pitch and formed so as to build up extra material at the threads. In some embodiments, a thread blank is molded separately from a core blank, and the two merged in a subsequent step inside a mold sized with tolerances close to those of the volume of the thread-core combination.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Layered Composite Material Bone Screw Geometry

Figure 1B:
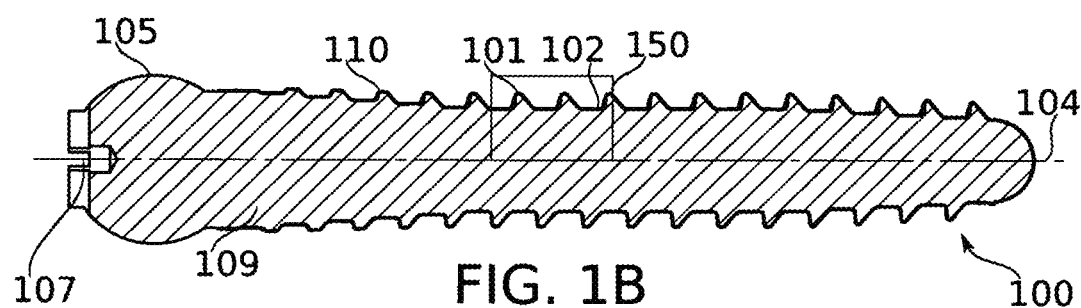
Figure 1C:
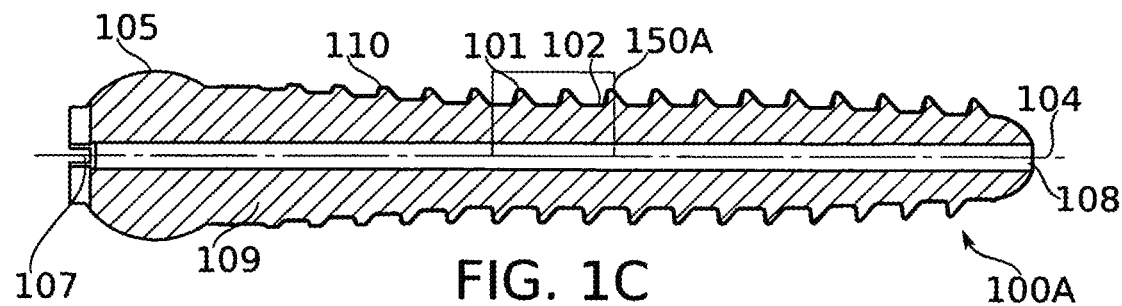
FIG. 1C schematically illustrates in cross-section a composite construction bone screw having a layered construction and a central cannula, according to some exemplary embodiments of the invention.
Figure 2A:
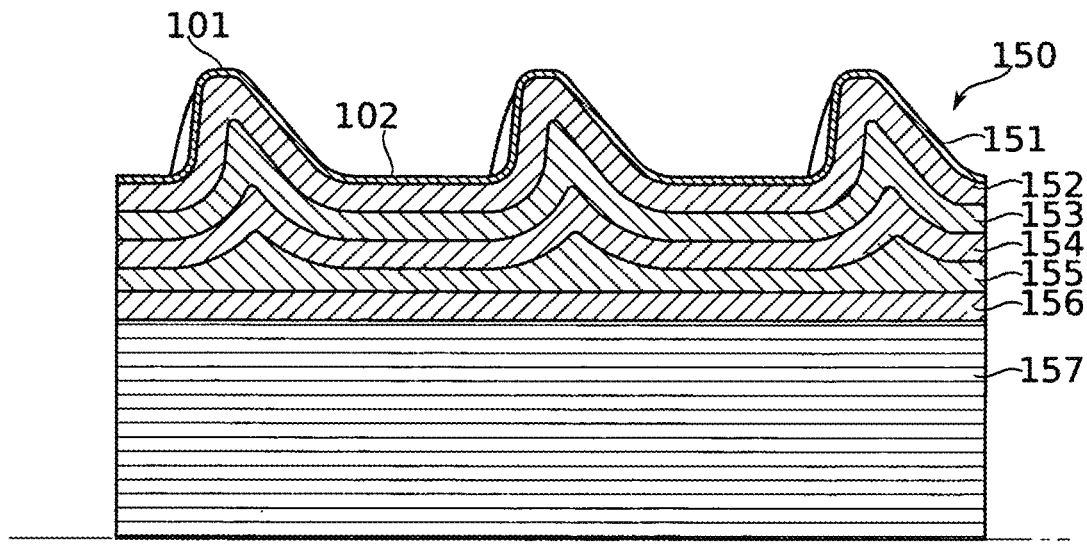
FIGS. 2A-2B and 3A-3B schematically illustrate in expanded view the layered structure of regions of the cross sections of FIG. 1B (FIGS. 2A-2B) and 1C (FIGS. 3A-3B), according to some exemplary embodiments of the invention.
Figure 2B:
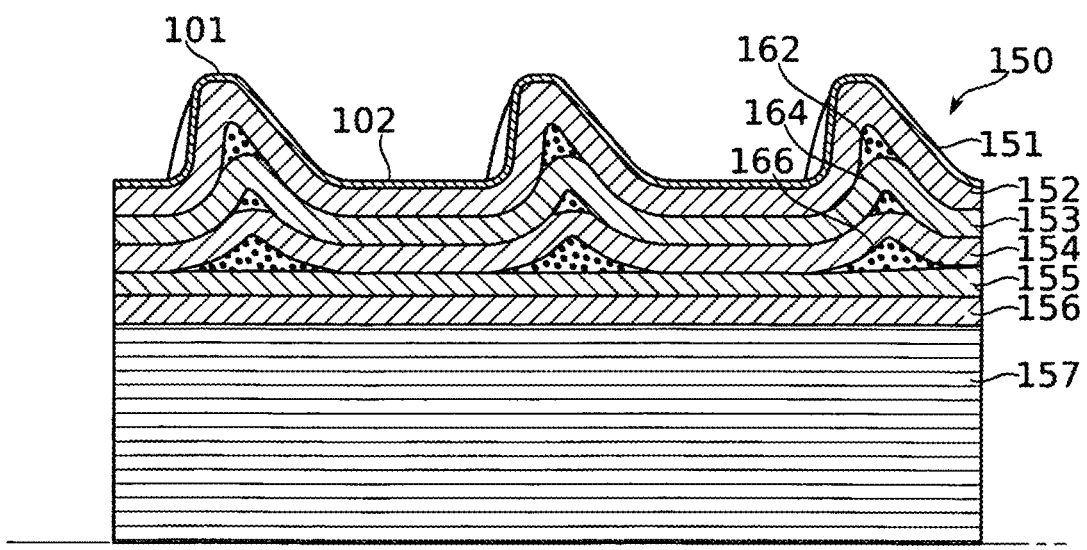
Figure 3A:
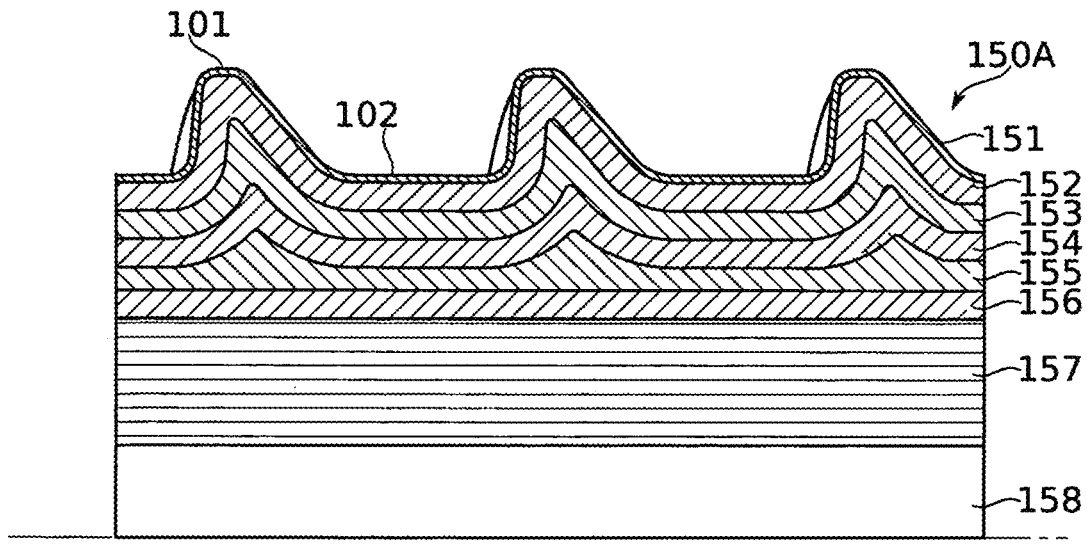
Figure 3B:
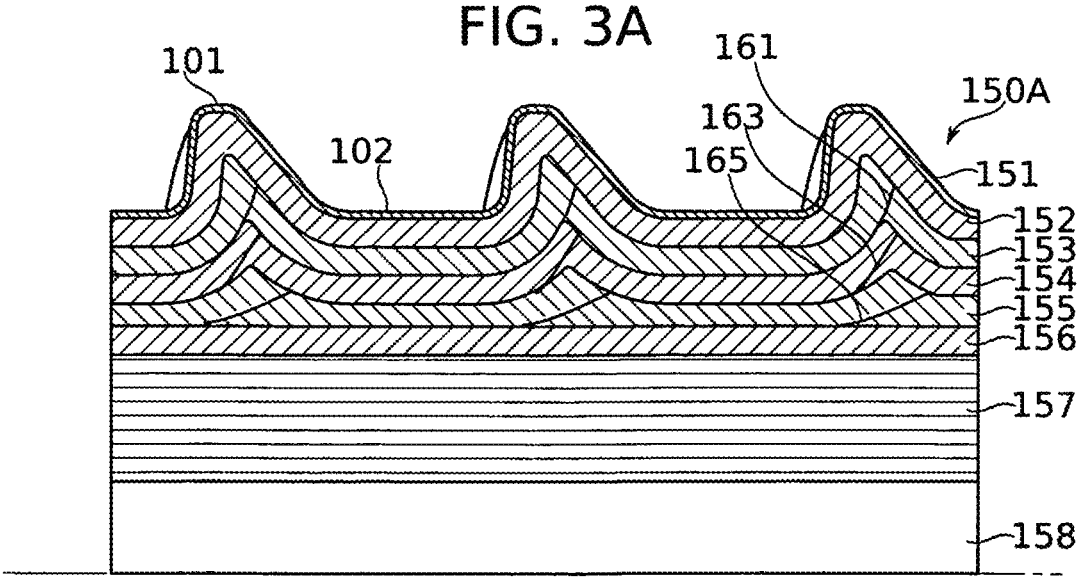

Reference is now made to FIGS. 1A-1B, which schematically illustrate in profile (FIG. 1A) and in cross-section (FIG. 1B) a composite construction bone screw 100 having a layered construction, according to some exemplary embodiments of the invention. Reference is further made to FIG. 1C, which schematically illustrates in cross-section a composite construction bone screw having a layered construction and a central cannula, according to some exemplary embodiments of the invention. FIG. 1B represents a cross-section along line A-A of bone screw 100, and FIG. 1C represents a cross section in the same plane of a cannulated bone screw 100A. Optionally, the cannula is, for example, of a diameter of between 1-3.5 mm, for example, 1 mm, 2 mm, 2.5 mm, 3 mm, or another larger, smaller, or intermediate diameter.

In some embodiments, a bone screw 100 comprises a head 105 and a shaft 103 extending along a central longitudinal axis 104 to a screw tip region 106. Head 105 is optionally formed with proximal region 107 shaped to receive torquing force for rotating the screw into a receiving bone plate and/or bone. Optionally a bone screw 100A is cannulated with a cannula 108. Optionally, the cannula 108 is used to guide the introduction of the screw to bone, for example, over a guidewire.

In some embodiments, the screw comprises a diameter (e.g., a diameter of the shank including the thread or a diameter of the shank without the thread) within a range of, for example, between 2.0-8.0 mm, or another longer or shorter diameter.

Optionally the screw has a larger outer diameter and/or larger core diameter nearer to head 105 (for example, 6.0 mm, 6.5 mm, 7.0 m, 8.0 mm, 8.5 mm, or another larger, smaller, or intermediate diameter), that decreases towards the distal end. Optionally, the screw has a longitudinal length within a range of, for example, between 10-65 mm, or another longer or shorter longitudinal length. The screw pitch optionally is in a range, for example, of between 0.8 mm and 2.0 mm, and/or within another range having the same, longer, shorter, and/or intermediate bounds.

In some embodiments, bone screw 100 comprises an internal body 109 of composite material construction (comprising, for example, CFR-PEEK and/or other materials such as materials added for radiopacity), and an outer layer 110 of metallic construction (for example, a foil, coating, tube, and/or shell of titanium and/or titanium alloy between 1-200 μm thick; or another layer construction).

In some embodiments, a region comprising portion 150 along the shaft 103 of the screw 100 comprises a plurality of screw thread windings, including raised thread portions 101, and the valleys of inter-thread portions 102.

Bone Screw Layers

Reference is now made to FIGS. 2A-2B and 3A-3B, which schematically illustrate in expanded view the layered structure of regions 150, 150A of the cross sections of FIG. 1B (FIGS. 2A-2B) and 1C (FIGS. 3A-3B), according to some exemplary embodiments of the invention.

Metallic, Partially Metallic, and/or Radiopaque Layers

Layer 151, in some embodiments, comprises a metallic outer layer. For descriptive convenience, layer 151 is represented as an uninterrupted monolayer (single ply layer). However, in some embodiments, layer 151 comprises any construction providing a metallic coating; for example: two or more metallic plies, a single metallic strip wound around itself (optionally overlapping itself at least in part), one or more shell pieces (for example, two longitudinally extending pieces fitted to one another and shaped to encase body 109), a continuous sheath, a plated and/or sputtered coating, and/or another construction of a thin metallic coating.

In some embodiments, layer 151 is made thick enough to provide the screw 100 with advantages of a metallic surface, for example toughness to resist surface wear and/or hardness to cut into a hole. However, in some embodiments, layer 151 is also thin enough to allow good formability over a core, such that fine structure (in particular, details of thread structure) can be manufactured by molding and/or pressing of a sheet- or tubular-formed starting material together with the body 109.

In some embodiments, layer 151 is thin enough to be substantially radiolucent, even though formed of metal (for example, titanium, titanium alloy, or stainless steel). For example, layer 151 is at least 50% radiolucent, at least 75%, 80%, 90%, 95%, 99%, or another greater, lesser, or intermediate degree of radiolucency (relative to a particular probe energy used in medical imaging; for example, hard X-rays). This is a potential advantage, for example, to reduce imaging artifacts due to the blockage and/or distortion of probing energies which can occur in the vicinity of highly radiopaque structures.

In some embodiments, a full or partial layer 152, lying immediately within layer 151, comprises material which increases radiopacity near the outer radius of the screw 100. This is a potential advantage, in particular when the outer layer 151 is so radiolucent that not only are artifacts reduced, but it becomes difficult to identify the screw in an image (for example a CT, MRI or other radiographic image). Adding radiopacity just inside the outer layer (rather than, for example, simply thickening the outer layer) provides a potential advantage by at least partially decoupling requirements for manufacturing and/or surface properties from requirements for radiopacity. For example, the added radiopaque material can be selected largely based on its specific radiopacity as such, with a reduced importance of its surface or other structural properties. In some embodiments, materials in layer 152 have a relatively high specific radiopacity (high linear attenuation coefficient) and may include, for—example, gold, platinum, rhenium, tungsten, tantalum, barium sulfate, and/or iodinated compounds. The radiopaque layer is optionally provided in any suitable form, for example, as a sheet, a deposited layer, powder, and/or discreet structures such as pellets and/or grains. In some embodiments, the linear attenuation coefficient is high over at least a portion of the range from 0.001 MeV to 1 MeV; for example, in a range from 50 keV to 500 keV. In some embodiments, a high linear attenuation coefficient comprises a linear attenuation coefficient at least 2×, 4×, 8×, or another larger, smaller, or intermediate factor higher than that of titanium.

In some embodiments, radiopaque material of layer 152 is interspersed with another substance, for example, a fiber-reinforced polymer composite material.

Optionally, use of materials with high linear attenuation coefficients allows thinner and/or sparser layers and/or amounts of radiopaque material to be provided to achieve the same level of radiopacity. Potentially, this provides an advantage to reduce interference of added radiopaque material with mechanical or other properties of the implant.

In some embodiments, a portion of the material of layer 152 (for example, radiopaque material, but optionally or additionally material composed as for layer 151) is attached to and/or integral with layer 151 (for example, pressed from a sheet portion of layer 151, welded to layer 151, or otherwise attached). In some embodiments, this portion of layer 152 is geometrically interlocked with fiber-reinforced polymer composite material. Potentially, this helps to keep a metallic outer layer 110 attached to a fiber-reinforced polymer body 109, for example, to resist torquing during insertion and/or removal of the screw 100 from a mounting hole.

While it is a potential advantage for radiopacity to be concentrated in outer layers of the screw (for identification of the outer limits of the screw itself), radiopaque layers are optionally placed anywhere within the screw body (for example, as one of and/or among layers 152-157).

Examples of Radiopacity Distribution and Properties

Figure 4:
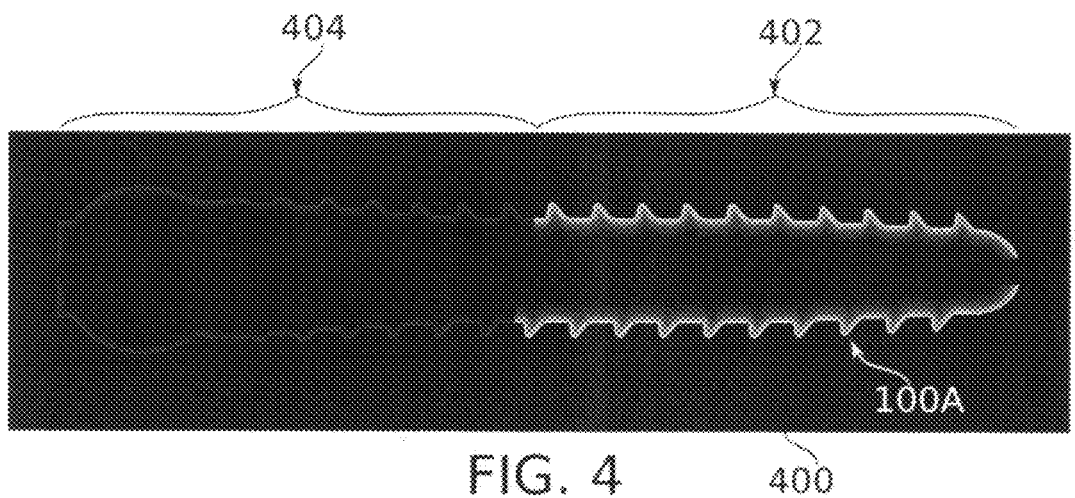
FIGS. 4-5 schematically illustrate the simulated radioimage appearances of bone screws with different arrangements of radiopaque materials, according to some exemplary embodiments of the invention.
Figure 5:
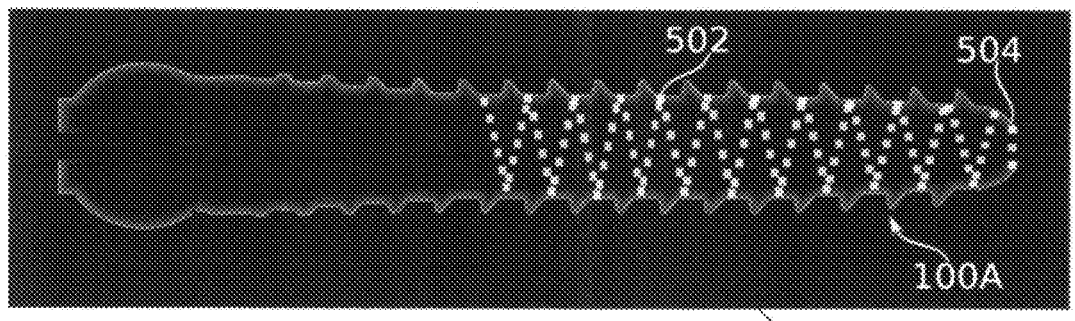

Reference is now made to FIGS. 4-5, which schematically illustrate the simulated radioimage appearances 400, 500 of bone screws 100A with different arrangements of radiopaque materials, according to some exemplary embodiments of the invention. While illustrated with respect to a cannulated screw 100A, it is to be understood that similar results are obtainable with non-cannulated screws 100.

In some embodiments, a bone screw 100A comprises a region 404 which is provided with a metallic surface (for example, titanium and/or titanium alloy) of sufficient thinness (for example, 60 μm or less) that it is mostly or even completely, radiolucent. Because of the rounded shape of the screw, the edges of this region will tend to be best defined under radioimaging, since the thickness of radiopaque material which must be penetrated is greatest where the curve of the screw is most nearly parallel to the direction of imaging radiation. Even so the screw edges may be indistinct, depending on imaging modality, energies, and/or environment. Nevertheless, in some embodiments, the whole bone screw is left to be substantially radiolucent in this fashion. Coverage with substantially radiolucent metal (radiolucent from any direction to at least 70%, 80%, 90%, or another greater, smaller, or intermediate amount of imaging radiation) is optionally over any percentage of the inner surface of the screw between 0% and 100%; for example, 0%, or at least 10%, 25%, 50%, 80%, or 100%.

In some embodiments, a bone screw 100A comprises a region 402 which is relatively radiopaque throughout a thickness near the surface of the bone screw. For example, an outer layer comprises a sheet or densely distributed powder of a radiopaque material such as gold, platinum, rhenium, tungsten, tantalum, barium sulfate, and/or iodinated compounds. In some embodiments, the relatively radiopaque layer extends underneath only a portion of the bone screw surface, for example, throughout a tip and/or shaft region. It is a potential advantage in particular to be able to clearly visualize tip position without the introduction of strong radiopacity artifacts, in order, for example, to identify potentially sensitive tissues (such as nervous tissue) in contact with to the screw. Optionally, a radiopaque layer extends underneath the whole surface of a bone screw. Coverage with a substantially radioopaque metal (radiopaque in at least one direction to block at least 70%, 80%, 90%, or another greater, smaller, or intermediate amount of imaging radiation) is optionally over any percentage of the inner surface of the screw between 0% and 100%; for example, 0%, or at least 10%, 25%, 50%, 80%, or 100%.

In some embodiments, radiopacity is concentrated to markers 502, 504, which are themselves substantially radiopaque (for example, opaque to at least 70%, 80%, 90%, or more of impinging imaging radiation), but are also diffusely spread at or just underneath the surface of the screw. Any useful pattern of spread is optionally chosen. For example, a metallic surface winding is optionally provided with markers 502 distributed along one edge, resulting in a pattern of radiopacity which follows at least a portion of the course of the edge (for example, follows the pitch of the screw).

Additionally or alternatively, locations of special interest in the screw are optionally marked; for example, markers 504 are provided at the tip of a screw 100A.

Fiber-Reinforced Composite Material Layers

Returning now to FIGS. 2A-3B: layers 152-156, in some embodiments, comprise layers of fiber-reinforced composite material (for example, CFR-PEEK) which extend along at least the threaded shaft region 103. In some embodiments, the layers comprise one or more plies of composite material tape (for example, pre-impregnated tape, or prepreg) wound around or otherwise assembled to screw body 109.

Prepreg tapes are available in the form of straight layers. During winding of each prepreg tape, the radius of curvature of the tape changes to conform to the current winding diameter of the core. During winding, the filaments at the inner portion of the tape (i.e., with the smallest radius) become slightly folded. Thus, upon application of torsion, the filaments at the outer portion of the tape are stretched and can resist the torsional moment, while the inner filaments are not yet stretched. The inner filaments receive tension upon exertion of higher torsional moments. In some embodiments, reducing the thickness (layering height on the screw) of the prepreg tape results in winding in which substantially more fibers are stretched earlier (i.e., upon application of lower torsional moment), for achieving more efficient torsional stiffness (for example, inner fibers begin to take up tension before outer fibers are damaged). Optionally the thickness of the prepreg for winding is in the range of 0.05 to 0.2 mm; for example, 0.1 mm or less.

Tape having directionally oriented fibers (for example, fibers running along the longitudinal length of the tape) is used, in some embodiments, to control the direction of fiber placement. The fibers are optionally oriented in a single direction, or in a plurality of selected directions (optionally, different directions are overlaid, interspersed, and/or interwoven). Each layer optionally comprises one or more windings of prepreg tape having substantially the same winding angle.

In some embodiments, tape with non-directional (and/or "spread directional") fiber orientation is used. Spread-directional orientation of fibers potentially increases resistance of the threads to damage by increasing the number of directions from which the fibers can shield the matrix from applied forces, by increasing the availability of fibers which anchor the thread, including anchoring fibers which extend in part through the radial depth of the screw, and/or by providing fibers which bridge potential cracks in any direction to resist crack spreading.

In some embodiments, spread-directional fiber orientation comprises a distribution of fiber orientations within a layer of the thread, wherein the fibers are circumferentially distributed throughout at least 30°, 45°, 60°, 90°, 135°, 180° (or another smaller or intermediate range) such that there is no discrete subrange of orientations which is unrepresented. The angular width of the discrete subrange is optionally greater than, for example, about 0.1°, 1°, 2°, 5°, or another larger or smaller subrange. As an exemplary frame of reference, longitudinally oriented fibers are optionally considered to have 0° orientation, horizontally (circumferentially) oriented fibers to have 90°/−90° orientation, and oblique (spiraling) fibers are oriented between 0° and 90° clockwise, and 0° and −90° counterclockwise.

A layer comprises, for example, a winding of pre-preg, or a layer of mold-injected material. In some embodiments, pre-preg and/or fibers are fragmented (for example, chopped), and optionally applied as a layer of fragmented material, and/or reformed into a continuous form and applied as a layer.

Optionally, a layer is defined by the radial extent of mutually intermingling threads. Optionally, the layer includes a portion within the thread body itself (radially positioned between the thread apex and base). Optionally, the layer includes a thread base region (a region just below the valley between threads); for example, a base region of up to 50% of the thread depth, up to 75% of the thread depth, up to 100% of the thread depth, or another larger, smaller, or intermediate depth.

In some embodiments, the relative distribution of fiber orientations is equal throughout the orientation distribution range. Optionally, the relative distribution follows another pattern, for example, with one or more peaks (for example, a Gaussian distribution). Insofar as different fiber orientations have different strengthening effects, it is a potential advantage to provide a non-equal distribution spread. For example, in some embodiments there is provided a relatively higher number of fibers which extend along the thread direction, compared to the angular density of thread-crossing fibers providing strength in other directions. It is noted in particular that relatively small angular changes from the strict thread orientation potentially create the largest difference in reinforcement properties. In some embodiments, the ratio of peak orientation density (for example, on the thread pitch direction) to an off-orientation density 15° away is, for example, a factor of about 2×, 4×, 10×, or another larger, smaller, and/or intermediate factor.

It is noted that finishing of a composite blank by machining has the potential to break (by cutting through) threads crossing longitudinally through the zone of layers which contribute to the thread. It is a potential advantage to preform a thread shape, even if some mechanical finishing is to be used, such that a population of thread-crossing (at least partially longitudinal) reinforcement fibers remains intact in the final product. Potentially, these thread-crossing fibers act to "root" the threads, for resistance of forces experienced during installation and/or operation.

It is also noted in particular that fibers which inhabit the thread-forming zone of a mold blank potentially experience distortion during molding. Although this can cause some reduction in their ability to shield from stress, this has a potential advantage for anchoring layers to one another. Potentially, this increases resistance to shear stresses.

Optionally, the fibers of the composite material are assembled to body 109 in a sequence of layers having orientations which alternately run substantially parallel to, and/or diagonal to longitudinal axis 104.

In some embodiments, one or more upper layers are wound at an angle which matches the thread angle. This is a potential advantage to provide torsional reinforcement and in particular stability in response to shear forces of insertion/ removal, while minimizing uneven distribution of tension due to fibers running across the threads 101, rather than along them. For example, fibers of layer 152 are wound to run in the same direction and with the same pitch as threads 101.

In some embodiments, layers (optionally, deeper layer) are wound to steeper angles. For example, fibers of layer 153 wind around the longitudinal axis 104 at a pitch angle of +45°, or at another angle, for example, an angle of between +30 to +60°. Optionally, fibers of the next layer (154, for example), wind at −45°, or at another pitch angle, for example, between −30° to −60°. Winding over the core at ±45° potentially provides for maximal torsional stiffness (compared, in particular, to longitudinal fibers), by maximizing fiber strain per degree of torsion.

Fibers of layer 155 are optionally laid along longitudinal axis 104, which potentially provides an advantage for providing longitudinal stiffness. Alternatively, fibers of layer 155 are laid at a positive angle again, for example, at the angle of the fibers of layer 153. Optionally, the layers continue to alternate among two or more fiber directions in layer 156, and/or any further number of oriented layers.

Optionally, layer 157 (comprising, for example, the deepest composite material layer of the composite body 109) comprises fibers oriented along the longitudinal axis 104 of the screw body. This provides a potential advantage for bending strength of the screw. In some embodiments, a central region 158 of the body 109 is cannulated (cannula 108), and free of composite material.

The construction described is of a particular potential advantage in the screw shaft 103; in the head 105 (where forces experienced are different, for example, due to internal torquing rather than external thread shearing), fiber direction is optionally differently distributed, for example, spiral all the way to the core.

It is to be understood that any order and/or direction of fiber layers is optionally provided.

Formation of Fiber Microstructure and Control of Stress Distribution

In some embodiments of the invention, the strength of the layered construction of shaft 103, in addition to being influenced by directions of winding, depends on the microstructural disposition of fibers with the layers at the conclusion of manufacturing steps such as winding and/or compression molding. For example, fibers laid initially straight within a core nevertheless potentially flex as a result of compression molding. In particular, compression molding producing an axial flow component (for example, between threads) tends to wrinkle and/or fold longitudinally aligned fibers. Threads 101 are another potential source of stress distribution anisotropies.

Control of Microstructure During Molding

In some embodiments, molding is arranged so that wave, wrinkle, and/or folding distortion of the inner fibers is avoided in the final product. In some embodiments, a core and/or core with outer layers is formed—relative to a mold which will receive it—such that it will not undergo axial distortion during the molding process. In some embodiments, the longitudinal axis of the core is sized to substantially the longitudinal length of the mold (for example, within a tolerance of 1 mm, 500 μm, 200 μm, 100 μm, 50 μm, or another greater, smaller, or intermediate tolerance, relative to the axial length of the mold). Optionally, the core is sized to a tolerance ensuring a size equal to or slightly less than the axial length of the mold, so that net axial material flow, if any, tends to lengthen, rather than compress, the fibers of the core.

Optionally, radial cross-sections of the part are also formed to substantially the shape and dimensions of the corresponding cross-section of the mold. For example, threads, screw heads, and/or other features of the part are sized to the mold, optionally within a tolerance such as that mentioned for the axial dimension, or another tolerance. In some embodiments, parts are molded in two or more pieces. For example, a straight-fiber core is molded with a simple mold shape that induces relatively little flow (or otherwise formed, for example, machined from a solid block of fused composite material). More complex shapes, such as threads, are optionally formed separately. Then the core piece and the complex piece or pieces are fused, for example, in an additional compression molding step. Optionally, the tolerance of the separate pieces to each other and/or to the mold is kept relatively small, to reduce flow during the fusion step. For example, tolerance is within 10 μm, 20 μm, 30 μm, 50 μm, or within another greater, smaller, or intermediate distance.

A potential effect of fitting the pre-molded part to the size of a mold—and then molding it—is for part changes due to the molding step to be primarily in the integration of composite material layers with one another, rather than in the shape of the part itself. Conditions of pressure and temperature potentially act to cause chemical bonding, local flow, and/or diffusion of composite matrix material to yield bonding among layers, without concomitant distortion of matrix fibers. A potential benefit of this is to increase part stiffness (for example, by preventing "slack" due to fiber deformation). In some embodiments, a maximal distance of flow (total, in an axial direction, and/or in a radial direction) during compression molding is, for example, less than 500 μm, 400 μm, 200 μm, 100 μm, 50 μm, or less than another greater, lesser, or intermediate distance. In some embodiments, fiber distorting axial flow in a compressive direction is prevented. Optionally, the maximal deviation from a predetermined orientation for fibers (e.g., maximum deviation from an average path orientation for a sample of nearby fibers of a particular winding direction) is less than 50 μm/mm, 25 μm/mm, 10 μm/mm, 5 μm/mm, or another greater, lesser, or intermediate maximal deviation.

Control of Microstructure by Laying Patterns of Prepreg

In some embodiments (with or without a plurality of molding steps used), layers are initially wound (or otherwise laid) with avoidance of air pockets (for example, by maintaining a sufficient winding tension).

In some embodiments, the shape of threads 101 are build up by direct compression of a substantially smooth surfaced (that is, unthreaded) starting core.

However, in some embodiments, prepreg tape is initially laid in layers of variable thickness such that the threads 101 are at least partially preformed before a step of compression molding. This is a potential advantage to maintain relative uniformity of stress and/or strain among fibers within each layer. To reduce a degree to which fibers are pre-stressed or unloaded by the formation of threads during compression molding, it is a potential advantage to lay prepreg with the material already substantially in its final position.

For example, one or more of layers 151-155 is provided with a thicker region at thread 101 by winding prepreg such that it partially overlaps itself (regions 163, 165 of FIG. 3B) and/or abuts itself at a protruding angle (region 165), along the shaft with a period of the thread pitch. Additionally or alternatively, thin (in width), feathered (growing thinner in thickness near one or both edges, for example as at region 165), and/or otherwise profile-shaped prepreg tape is used to preferentially build up layer thickness in thread regions of the shaft, Optionally, a profile used in winding among deeper layers is broader and/or lower in height than a profile used in winding among more shallow layers Optionally, relatively uniform layers of 45°-angled fiber are interspersed with layers of thread-building prepreg material wound at the angle of the threads, for example as shown at sub-layers 162, 164, and 166 of FIG. 2B. For example, layer 155 is optionally comprised of a plurality of winding directions, including one at one of ±45°, and one (layer 166) at the thread pitch.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A fiber-reinforced composite material bone screw comprising:
    a screw core comprising fiber-reinforced polymer matrix composite material having a first fiber arrangement; and
    a thread region circumferentially surrounding the screw core at least along a threaded shaft of the screw, the thread region comprising fiber-reinforced polymer matrix composite material having a second fiber arrangement;
    wherein the fibers of the fiber-reinforced polymer matrix composite material of the thread region comprise at least a first fiber population and a second fiber population, wherein at least 10% of the fibers of said first population pass at an angle of at least 10 degrees relative to fibers of said second fiber population; said at least first and second populations interspersed with each other and within said polymer matrix of the thread region; and
    wherein the thread region is formed by compression molding.

2. The bone screw of claim 1, wherein particles of powdered radiopaque marker material are distributed within the polymer matrix of the thread region, said particles of powdered radiopaque marker material arranged circumferentially around at least a portion of the thread region, and beneath a threaded surface of the screw core.

3. The bone screw of claim 2, wherein the radiopaque marker material comprises at least one from the group consisting of gold, platinum, rhenium, tungsten, tantalum, barium sulfate, and/or iodinated compounds.

4. The bone screw of claim 2, wherein the radiopaque marker material is in a powdered form, the particles of the powder being less than 200 μm in diameter.

5. The bone screw of claim 2, wherein the radiopaque marker material is at least 10 μm from the outer surface of the screw core.

6. The bone screw of claim 2, wherein the radiopaque marker material extends circumferentially around at least 70% of the circumference of the portion of the screw core.

7. The bone screw of claim 2, wherein the radiopaque marker material extends circumferentially entirely around the circumference of the portion of the screw core.

8. The bone screw of claim 2, comprising a metallic outer layer circumferentially surrounding the particles of radiopaque material.

9. The bone screw of claim 8, wherein the material of the metallic outer layer comprises at least one of the group comprising titanium and titanium alloy.

10. The bone screw of claim 9, wherein an inner portion of the metallic outer layer comprises the radiopaque marker material in a sheet form.

11. The bone screw of claim 8, wherein the radiopaque marker material comprises a material having a greater linear attenuation coefficient than the outer material of the metallic outer layer.

12. The bone screw of claim 2, wherein the radiopaque marker material is concentrated along at least one path following a helical path of the thread of the threaded shaft.

13. The bone screw of claim 2, wherein the radiopaque marker material comprises at least one radiopaque region at a screw tip at one end of a longitudinal axis of the bone screw.

14. The bone screw of claim 1, wherein said fibers of said thread region also alternately extend radially inward and outward.

15. The bone screw of claim 1, wherein said fibers of said thread region comprise a substantially continuous distribution of orientations relative to a helical path of said screw, with no gaps of missing orientations wider than about 5°.

16. The bone screw of claim 1, wherein said fibers of said thread region comprise a substantially continuous distribution of orientations relative to a helical path of said screw through all angles tangential to the screw core.

17. The bone screw of claim 1, wherein said fibers of said thread region comprise a substantially continuous distribution of orientations relative to a helical path of said screw through all angles.

18. The bone screw of claim 1, wherein all fiber orientations within the thread region are about equally represented.

19. The bone screw of claim 1, wherein fibers extending through the thread region also extend through a thread base region comprised of said composite material extending continuously between the thread windings.

20. The bone screw of claim 1, wherein fibers of said first fiber population and said second fiber population are dispersed at various directions with respect to a winding direction of said thread.

21. The bone screw of claim 1, wherein fibers of said thread region comprise a population of fiber lengths passing within the thread region which is substantially omnidirectional at least circumferentially with respect to a helical path of the thread region.

22. The bone screw of claim 2, wherein said particles of powdered radiopaque marker material are included in a layer within the polymer matrix.

23. The bone screw of claim 2, wherein said particles of powdered radiopaque marker material are included in discreet structures within the polymer matrix of said thread region.

24. The bone screw of claim 23, wherein said discreet structures are one of pellets and grains.

25. The bone screw of claim 1, wherein said thread region includes at least one layer of windings of prepreg tape, each layer of windings having substantially the same winding angle.

26. The bone screw of claim 1, wherein at least 10% of the fibers of said first population pass at an angle of less than 90 degrees relative to the fibers of said second fiber population.

27. The bone screw of claim 1, wherein the fiber-reinforced polymer matrix extends between a thread valley and a thread peak.

* * * * *